United States Patent
Gonzalez et al.

(10) Patent No.: US 9,725,501 B2
(45) Date of Patent: *Aug. 8, 2017

(54) TWO-STAGE ULTRAFILTRATION/DIAFILTRATION

(71) Applicant: GRIFOLS THERAPEUTICS INC., Research Triangle Park, NC (US)

(72) Inventors: Martin Gonzalez, Clayton, NC (US); Woody D. Wood, Selma, NC (US); Fred H. Earp, Selma, NC (US)

(*) Notice: Subject to any disclaimer, the term of this patent is extended or adjusted under 35 U.S.C. 154(b) by 346 days.

This patent is subject to a terminal disclaimer.

(21) Appl. No.: 14/294,460

(22) Filed: Jun. 3, 2014

(65) Prior Publication Data
US 2014/0343255 A1    Nov. 20, 2014

Related U.S. Application Data

(63) Continuation of application No. 12/937,454, filed as application No. PCT/US2009/040499 on Apr. 14, 2009, now Pat. No. 8,772,461.

(60) Provisional application No. 61/045,233, filed on Apr. 15, 2008, provisional application No. 61/118,001, filed on Nov. 26, 2008.

(51) Int. Cl.
| C07K 1/30 | (2006.01) |
| C07K 1/34 | (2006.01) |
| C07K 1/36 | (2006.01) |
| C07K 16/06 | (2006.01) |

(52) U.S. Cl.
CPC .............. *C07K 16/065* (2013.01); *C07K 1/30* (2013.01); *C07K 1/34* (2013.01); *C07K 1/36* (2013.01)

(58) Field of Classification Search
None
See application file for complete search history.

(56) References Cited

U.S. PATENT DOCUMENTS

| 4,396,608 A | 8/1983 | Tenold |
| 4,404,132 A | 9/1983 | Mitra |
| 4,990,252 A | 2/1991 | Tomaschke et al. |
| 5,112,812 A | 5/1992 | Samuelsson et al. |
| 5,177,194 A | 1/1993 | Sarno et al. |
| 5,886,154 A | 3/1999 | Lebing et al. |
| 5,945,098 A | 8/1999 | Sarno et al. |
| 6,096,872 A * | 8/2000 | Van Holten ............ A61L 2/0017 424/173.1 |
| 6,406,631 B1 | 6/2002 | Collins et al. |
| 7,422,899 B2 | 9/2008 | Elenbaas et al. |
| 2005/0053598 A1 | 3/2005 | Burke et al. |
| 2006/0051347 A1 | 3/2006 | Winter |
| 2006/0088883 A1 | 4/2006 | Smider et al. |
| 2006/0149042 A1 | 7/2006 | Konstantinov |
| 2007/0049733 A1 | 3/2007 | Zurlo et al. |
| 2007/0237762 A1 | 10/2007 | Winter |

FOREIGN PATENT DOCUMENTS

| EP | 0447585 | 5/1995 |
| EP | 1696640 | 6/2006 |
| EP | 1314437 | 6/2014 |
| RU | 2155069 | 8/2000 |
| WO | WO-97/45140 | 12/1997 |
| WO | WO-99/64462 | 12/1999 |
| WO | WO-02/096457 | 12/2002 |
| WO | WO-2004/001007 | 12/2003 |

OTHER PUBLICATIONS

International Search Report dated Aug. 26, 2009 issued in PCT/US2009/040499.
Lal Baruah et al., "Purification of Monoclonal Antibodies Derived From Transgenic Goat Milk by Ultrafiltration," Biotechnology and Bioengineering, vol. 93, No. 4, Mar. 5, 2006, pp. 747-754.
Product Data Sheet on Centrifugal Devices for Ultrafiltration and Microfiltration of Pall Life Sciences, 2003, available online at http://wolfson.huji.ac.li/purification/PDF/dislysis/PALL_CentrifugalDevice.pdf pp. 1-12.
Cheang et al., "A two stage ultrafiltration process for fractionation of whey protein isolate"; Journal of Membrane Science 231 (2004), pp. 159-176.
Kavonian et al., "Ultrafiltration: Trends in Sample Prep", G&P magazine: vol. 6, No. z, Jan./Feb. 2006, pp. 24-29.
McCue et al., "Three Generations of Immunoglobulin G preparations for Clinical Use," Reviews of Infections Diseases, vol. 8, Supplement 4 (Jul.-Aug. 1986): pp. S374-S381.
Product information on Pepsin available on the web page of the provider SIGMA-ALDRICH (http://www.sigmaaldrich.com/life-science/metabolomics/enzymeexplorer/analytical-enzymes/pepsin.printerview.html), retrieved on Jul. 11, 2013, pp. 1-4.
Roe, "Protein Purification Techniques: A practical approach (Practical Approach Series)", Oxford University Press, USA, Second Edition, 2001, pp. 111-115.
Rubin et al., "Selecting the Right Ultrafiltration Membrane for Biopharmaceutical Applications; Pharmaceutical Technology Europe," 14; 39-48 Advanstar Publication; Reprint of Dec. 2002.

\* cited by examiner

*Primary Examiner* — Daniel E Kolker
*Assistant Examiner* — James Rogers
(74) *Attorney, Agent, or Firm* — Womble Carlyle Sandridge & Rice LLP.; Scott R. Breining (57) ABSTRACT

The present invention provides a method for concentrating a protein, in particular a method for concentrating a plasma product, in particular IgG, using glycine in a two-stage ultrafiltration/diafiltration approach.

15 Claims, 10 Drawing Sheets

TWO-STAGE ULTRAFILTRATION/DIAFILTRATION

CROSS-REFERENCE TO RELATED APPLICATIONS

This application is a continuation of U.S. patent application Ser. No. 12/937,454 filed May 20, 2011, which is a national phase of International Application PCT/US09/40499, filed Apr. 14, 2009, which claims priority under 35 USC §119 to U.S. Provisional Application No. 61/045,233, filed Apr. 15, 2008 and U.S. Provisional Application No. 61/118,001 filed Nov. 26, 2008, each of which is herein incorporated by reference in its entirety.

FIELD OF THE INVENTION

The present invention relates to methods for preparing a concentrated protein formulation and compositions comprising such a preparation, in particular to methods for preparing a concentrated plasma product formulation, in particular to methods for preparing and compositions comprising concentrated IgG.

BACKGROUND OF THE INVENTION

Typically, only one type of ultrafiltration membrane is used to achieve final concentrations of plasma products for formulation. Research demonstrates that cassette ultrafiltration can produce higher concentrations. However, due to higher viscosity and high protein concentration, product recovery is greatly reduced as the membrane tends to clog or foul. Studies also have shown that targeting high concentrations prevent membrane recovery post cleaning.

Accordingly, it would be desirable to provide a method for concentrating a plasma product to achieve higher final concentrations while minimizing yield loss and impact on processing time.

SUMMARY OF THE INVENTION

In one aspect, the present invention provides a method for concentrating a protein of a solution comprising the protein. The method comprises:
a) ultrafiltering the solution using a first membrane to form a first retentate solution comprising the protein at a first concentration, wherein the first membrane has a molecular weight cutoff sufficient to retain at least a portion of the protein present in the solution;
b) diafiltering the first retentate solution with an aqueous solution using the first membrane to form a second retentate solution comprising the protein at about the first concentration;
c) formulating the second retentate comprising the diafiltered protein with glycine and adjusting the pH; and
d) ultrafiltering the second retentate solution using a second membrane to form a final retentate solution comprising the protein at a second concentration, wherein the second membrane has a molecular weight cutoff of about twice the molecular weight cutoff of the first membrane, wherein the second concentration is greater than the first concentration.

In another aspect, the present invention provides a method for concentrating a protein of a solution comprising the protein. The method comprises:
a) ultrafiltering the solution using a first membrane to form a first retentate solution comprising the plasma product at a first concentration of about 5%, wherein the first membrane has a molecular weight cutoff sufficient to retain at least about 90% of the plasma product;
b) diafiltering the first retentate solution using the first membrane with water to form a second retentate solution comprising the plasma product at about the first concentration;
c) formulating the about 5% diafiltered plasma product of step b) to about 0.16 to about 0.30 M glycine, wherein the formulating further comprises adjusting pH to about 4.3; and
d) ultrafiltering the second retentate solution using a second membrane to form a final retentate solution comprising the plasma product at a second concentration of about 19 to about 21%, wherein the second membrane has a molecular weight cutoff of about twice the molecular weight cutoff of the first membrane, wherein the second concentration is greater than the first concentration.

DETAILED DESCRIPTION OF THE INVENTION

In accordance with the present invention, it has been surprisingly discovered that a progressive two stage ultrafiltration/diafiltration approach to concentrating a protein can provide for compositions comprising the concentrated protein. For example, in some embodiments, the present invention provides a novel concentration concept to achieve a higher final plasma product formulation that can be suited for therapeutic or prophylactic use and/or administration by a variety of methods including subcutaneous injections.

As used herein, the term "protein" is intended to include any recombinant or purified polypeptide including, but not limited to, a naturally-occurring, modified, or synthesized polypeptide, and multimers, fragments (e.g., a biologically active fragment), or variants thereof.

The protein can be derived from a human or a non-human including, but not limited to, dogs, cats, pigs, horses, cows, birds, fish, amphibians, reptiles, transgenics, etc.

The term "biologically active fragment" refers to a fragment of a protein that retains at least one of the functions of the protein from which it is derived. For example, a biologically active fragment of an antibody includes an antigen-binding fragment of the antibody; a biologically active fragment of a receptor includes a fragment of the receptor that can still bind its ligand; a biologically active fragment of a ligand includes that portion of a ligand that can still bind its receptor; and a biologically active fragment of an enzyme includes that portion of the enzyme that can still catalyze a reaction catalyzed by the full length enzyme.

In one embodiment, the protein is a plasma product.

As used herein, the term "plasma product" refers to a protein that can be generally characterized as a component of blood or blood fraction of a human or a non-human. For example, the γ-globulin fraction of blood comprises proteins such as immunoglobulins and C-reactive protein. The α1-globulin fraction contains proteins such as α1-acid glycoprotein, α1-antitrypsin, and α1-lipoprotein. The α2-globulin fraction contains proteins such as α2-macroglobulin, haptoglobulin, ceruloplasmin, and group-specific complement. The β-globulin fraction contains proteins such as transferrin, hemopexin, β1-lipoprotein, β2-microglobulin, and complement components.

In some embodiments, the protein to be concentrated is an antibody. The term "antibody" as used herein, includes, but is not limited to, polyclonal antibodies, monoclonal antibodies, antibody compositions with polyepitope specificities, bispecific antibodies, and diabodies. The antibodies can be whole antibodies, e.g., of any isotype (e.g., IgG, IgA, IgE, IgM, IgD), or antigen binding fragments thereof. Generally, an antibody fragment comprises the antigen-binding and/or the variable region of an intact antibody. Thus, the term antibody fragment includes segments of proteolytically cleaved or recombinantly prepared portions of an antibody molecule that are/can selectively bind to a selected protein. Non-limiting examples of such proteolytic and/or recombinant fragments include Fab, F(ab')$_2$, Fab', Fv, and single chain antibodies (scFv) containing a V[L] and/or V[H] domain joined by a peptide linker. The scFvs may be covalently or noncovalently linked to form antibodies having two or more binding sites.

Immunoglobulins can be prepared from the plasma of unselected normal donors, while hyperimmunoglobulins can be prepared from the plasma of donors with high antibody titers against specific antigens. These hyperimmune donors may be identified during convalescent periods after infection or transfusion, or they may be specifically immunized to produce the desired antibodies.

In some embodiments, the plasma product is immunoglobulin G (IgG). A process for the purification of antibodies from human or other sources is disclosed in U.S. Pat. No. 5,886,154 to Lebing et al., which is incorporated herein by reference in its entirety.

In addition to albumin and immunoglobulins, lipoproteins are another class of blood components. For example, three classes of lipoproteins, α1-lipoprotein, pre-β-lipoprotein, and β1-lipoprotein, can be distinguished in human blood, for example according to their electrophoretic behavior. Apolipoproteins, which are the protein component of lipoproteins include apolipoproteins A-1, A-2, A-4, B-48, B-100, C, D, and E.

A number of blood proteins function as carriers including those which transport metal ions, such as the iron-binding protein, transferrin, and the copper-binding protein, ceruloplasmin, and 9.5 S-α1-glycoprotein. Prealbumin and the thyroxin-binding globulin transport the thyroid hormone, and transcortin transports the steroid hormones. Hemoglobin is eliminated from the circulation by haptoglobin, and heme is bound to hemopexin. The retinol-binding globulin binds vitamin A. The transcobalamins I, II, and III bind vitamin B12. Gc-globulin binds vitamins D2 and D3.

A number of blood proteins are enzymes, pro-enzymes, or enzyme inhibitors. Blood proteins which are enzymes (e.g., proteinases) include, for example, cholinesterase, ceruloplasmin, plasminogen, protein C, and β2-glycoprotein I. Pro-enzymes (i.e., zymogens) are converted to enzymes by the action of specific enzymes. Proteinase inhibitors control this process by reducing or eliminating the activity of these specific enzymes. The major proteinase inhibitor found in human blood is al-antitrypsin (i.e., α1-proteinase inhibitor; α1-trypsin inhibitor, prolastin) which protects tissues from digestion by elastase. Another class of proteinase inhibitors found in human blood are the antithrombins, such as antithrombin III, which prevent the effects of thrombin. Still another proteinase inhibitor found in human blood is C1-esterase inhibitor, which reduces or eliminates the activity of C1-esterase, which is the activated first component of complement, C1. Other blood proteins which are enzyme inhibitors include α1-antichymotrypsin, inter-α-trypsin inhibitor, α2-macroglobulin, and α2-antiplasmin.

Some blood proteins are involved with the clotting process (i.e., coagulation factors). Blood clots are formed by an enzymatic cascade, with the activated form of one factor catalyzing the activation of the next factor which results in a large amplification and a rapid response to trauma. Examples of inactivated and activated clotting factors include, for example, XII and XIIa; XI and XIa; IX and IXa; X and Xa; VII and VIIa; II (prothrombin) and Ia (thrombin); I (fibrinogen) and Ia (fibrin). Other clotting factors include kininogen, kallikrein, and factors VIII, VIIIa, V, Va, XIII, and XIIIa. A number of clotting factors are also referred to as vitamin K dependent proteins, including, for example, Factor II (prothrombin), Factor VII, Factor IX, Factor X, Protein C, and Protein S.

Some blood proteins are complement components and together comprise the complement system, which lyses microorganisms and infected cells by forming holes in their plasma membrane. More than 15 complement proteins are known, including C1, C1q, C1r, C1s, C2, C3, C4, C5, C6, C7, C8 and C9.

Examples of glycoproteins which can be purified from human blood include α1-acid glycoprotein, α2-glycoprotein, α2-macroglobulin, α2-HS-glycoprotein, α1-antichymotrypsin, α1-antitrypsin, fibrinogen, fibronectin, pre-albumin, hemopexin, haptoglobin, transferrin, ceruloplasmin, many clotting factors, and many components of the complement system.

In one aspect, the present invention provides a method for concentrating a protein of a solution comprising the protein. The method comprises the following steps:

a) ultrafiltering the solution using a first membrane to form a first retentate solution comprising the protein at a first concentration, wherein the first membrane has a molecular weight cutoff sufficient to retain at least a portion of the protein present in the solution;

b) diafiltering the first retentate solution with an aqueous solution using the first membrane to form a second retentate solution comprising the protein at about the first concentration;

c) formulating the second retentate comprising the diafiltered protein with glycine and adjusting the pH; and d) ultrafiltering the second retentate solution using a second membrane to form a final retentate solution comprising the protein at a second concentration, wherein the second membrane has a molecular weight cutoff of about twice the molecular weight cutoff of the first membrane, wherein the second concentration is greater than the first concentration.

In one embodiment, the first concentration is at least about 1% protein (w/v), illustratively, about 1% to about 15%, about 2% to about 12%, about 3% to about 10%, about 4% to about 8%, and about 5% to about 6% protein (w/v). In another embodiment, the first concentration is about 5% protein (w/v).

In one embodiment, the first membrane has a molecular weight cutoff sufficient to retain at least 90% of the protein present in the solution.

In another embodiment, the aqueous solution is cold water for injection (CWFI).

In other embodiments, in step c), the diafiltered protein is formulated to about 0.16 to about 0.30 M glycine and the pH is adjusted to about 4.3.

In one embodiment, the second concentration is about 19% to about 21%.

In some embodiments, the protein is IgG.

I. The Solution

The solution comprising the protein can be a dilute protein-containing solution, wherein the protein contained in the solution is to be concentrated prior to use in downstream applications. For example, following concentration of the protein in accordance with the present invention, the final retentate solution comprising the concentrated protein may be used for preparing formulations suitable for providing an injection (e.g., subcutaneous, intramuscular, intravenous) of the protein to a subject (e.g., a human or a non-human including, but not limited to, dogs, cats, pigs, horses, cows, birds, fish, amphibians, reptiles, etc.). Preferably, the solution comprising the protein to be concentrated is a product of at least one upstream purification scheme that yields the solution (e.g., a dilute protein-containing solution) having a desired level of protein purity and viral clearance. In one embodiment, the protein purity of the solution is at least about 90%, 92%, 94%, 96%, 98%, 99%, or more.

In some embodiments, the solution comprising the protein to be concentrated is an eluate or a flow-through from a chromatography of a starting material comprising the protein.

For example, chromatography techniques for purifying a plasma product are well known in the art and include, e.g., ion exchange chromatography (e.g., anion exchange), hydrophobic interaction chromatography, affinity chromatography, immuno-affinity chromatography, and size-exclusion chromatography. The starting material can be an alcohol/pH precipitated plasma fraction such as, for example, a Cohn fraction, which is known to one of ordinary skill in the art. Preferably, the Cohn fraction is Fraction II+III, or a fraction obtained by subfractionation of II+III (e.g., Fraction II). A source of the starting material can be any source comprising the plasma product including, but not limited to, ascites fluid, tissue culture media containing the plasma product, human plasma fractions, and animal plasma fractions.

In one embodiment, the solution comprising the protein to be concentrated is obtained following anion exchange chromatography of the starting material. In another embodiment, several anion exchange resin combinations are utilized depending on selectivity of the resins. For example, the anion exchange resins can be chosen for their ability to selectively remove the impurities found in the starting material (e.g., an alcohol/pH precipitated plasma fraction) comprising a plasma product. In one embodiment, the alcohol/pH precipitated plasma fraction is Cohn Fraction II+III or Fraction II paste.

In one embodiment, the starting material comprises the plasma-product IgG. Preferably, the starting material (e.g., Fraction II+III paste) comprising IgG to be purified is passed through two anion exchange chromatography columns linked in series (e.g., combinations of Pharmacia Biotech Q & ANX resins and/or E. Merck TMAE Fractogel) to provide the solution comprising the plasma-product. The anion exchangers can be chosen for ability to remove IgA, IgM, albumin and other remaining protein impurities from the starting material. After loading, the columns can be washed with equilibration buffer. The flow through and wash fraction can be collected as purified IgG. Both columns can be equilibrated with the same buffer and at the same pH. Prior to chromatography, the starting material can be subjected to other processes.

Ion exchange chromatography takes advantage of surface distribution and charge density on both the protein and the ion exchange media. Without being held to a particular theory, it is believed that the anion exchange resin presents a positively charged surface. The charge density is specific to the resin and generally is independent of pH (within the working range of the resin). A typical anion exchanger will bind proteins which have a net negative charge (i.e. when the pH of the solution is above the isoelectric point of the protein). In reality, the surface of a protein does not present a singular charge; rather it is a mosaic of positive, negative, and neutral charges. Surface structure is specific to a given protein and will be affected by solution conditions such as ionic strength and pH. This uniqueness can be exploited to establish specific conditions where individual proteins will bind or release from the anion exchange resin. By establishing these conditions, proteins with only slightly differing surface or charge properties can be effectively separated with high yield (e.g., >95%).

Improvements in the structure of chromatography resin supports have made large scale chromatography a practical alternative to more conventional purification methods. Rigid resins allow large volumes to be processed rapidly (<5 hours), and high ligand density gives the increased capacity necessary for large volume processing.

In another embodiment, the solution comprising the protein to be concentrated is a solvent/detergent-treated solution comprising the protein. For example, IgG can be isolated from solubilized Cohn fraction II and treated with a solvent/detergent system for viral inactivation. Solvent/detergent treatment systems include e.g., tri-n-butyl-phosphate/sodium cholate (TNBP/sodium cholate) and TWEEN/tri-n-butyl phosphate (TNBP).

In one embodiment, the solvent/detergent is TNBP/sodium cholate. For example, a Cohn Fraction II+III or II solution can be adjusted to a final concentration of 0.3% tri-n-butyl phosphate (TNBP) and 0.2% sodium cholate. After the addition of solvent (TNBP) and detergent (sodium cholate), the Cohn Fraction II+III or II solution can be heated to an optimal temperature, e.g. 30° C., and maintained at that temperature for a suitable period of time such as, e.g., not less than about 6 hours. After the solvent/detergent treatment step, which involves viral inactivation, the reactants can be removed by precipitation and filtration, e.g., through a series of filters graduated in porosity to a 0.2 μm filter to form a solution comprising a plasma product (e.g., IgG).

II. The First Membrane

In accordance with the two-stage progressive filtration approach of the present invention, the solution comprising the protein is ultrafiltered using the first membrane to form the first retentate having the protein at the first concentration. Generally, the retention of a target molecule by an ultrafiltration membrane is determined by a variety of factors including the molecular weight of the plasma product to be concentrated. Other factors such as e.g., molecular shape, electrical charge, and operating conditions can influence the determination of the appropriate molecular weight cutoff of the membrane. Preferably, the first membrane has a molecular weight cutoff sufficient to retain at least a portion of the protein present in the solution comprising the protein, for example at least 10% to at least about 90% or more of the protein present in the solution.

In some embodiments, wherein the protein to be concentrated is IgG having a molecular weight of about 150 kilodaltons (kDa), the solution comprising the IgG is ultrafiltered using a first membrane having a molecular weight cutoff of no greater than about 100 kDa, illustratively, no greater than about 100, about 75, and about 50 kDa to form a first retentate solution comprising the plasma product. In one embodiment, the first membrane has a molecular weight cutoff of no greater than about 50 kDa.

Following ultrafiltration using the first membrane, preferably, the first concentration of the protein in the first retentate solution is about 5% protein (w/v). Thus, if the concentration of the protein in the solution is less than about 5% protein (w/v), ultrafiltration of the solution using the first membrane is sufficient to form the first retentate solution comprising about 5% protein (w/v).

The first membrane can be any suitable ultrafiltration membrane, which can be selected based on its rejection characteristics for the protein to be concentrated in accordance with the present invention. In some embodiments, the first membrane is made of polyethersulfone (PES) or regenerated cellulose. Non-limiting examples of the first membrane include BIOMAX™ and Ultracel ultrafiltration membrane of Pellicon module, PT and PL ultrafiltration membranes of Prostak module, PT, PL, and Helicon ultrafiltration membrane of Spiral Wound Ultrafiltration module, manufactured by Millipore Co., Sartocon™, and Ultrasart™ ultrafiltration membrane, manufactured by Sartorius AG, NOVA™, OMEGA™, ALPHA™, REGEN™, SUPOR™ ultrafiltration membranes, manufactured by Pall Co., Filmtec™ ultrafiltration membrane, manufactured by Dow Chemical Co., and Kvick™ ultrafiltration membrane, manufactured by Amersham Pharmacia Biotech Inc. In one embodiment, the first membrane is a PES membrane having a molecular weight cutoff of 50 kDa, wherein the protein is IgG.

Generally, a batch type or a continuous type of ultrafiltration process is carried out according to the structure of the filtration membrane and the filtering device. And, purified water can be continuously fed into retentate to keep up a constant volume. In one embodiment, the solution is ultrafiltered using the first membrane using a continuous cross-flow type of ultrafiltration. In another embodiment, the ultrafiltration process is carried out at about 2° C. to about 15° C.

In one embodiment, ultrafiltering using the first membrane is based on tangential flow technology, which is well known in the art. Tangential flow produces a "sweeping" action using the membrane surface thereby keeping the retained macromolecules in the retentate phase from accumulating at the membrane surface, thus minimizing concentration polarization and membrane fouling. In some embodiments, the solution comprising the protein is re-circulated across the top of the membrane i.e., "tangentially" to the membrane surface.

III. Diafiltering

Following ultrafiltering using the first membrane, the first retentate solution comprising the protein at the first concentration (e.g., about 5% protein (w/v)), is diafiltered with an aqueous solution using the first membrane to form a second retentate solution comprising the protein at substantially the first concentration in order to remove any traces of the chromatography buffers. The aqueous solution can be water (e.g., cold water for injection (CWFI)) or a suitable buffer.

Diafiltering the first retentate can be a continuous or a discontinuous process. In the method of continuous diafiltration, which is also referred to as constant volume diafiltration, the concentration of the protein in the retentate does no change substantially during the diafiltration process. Thus, the retentate volume and the protein concentration do not change significantly, if at all, during the diafiltering step.

In one embodiment, diafiltering the first retentate solution using the first membrane comprises using a continuous or discontinuous diafiltration process by washing through at least 1, 2, 3, 4, 5, 6, and 7 retentate volumes (i.e., at least about 1, 2, 3, 4, 5, 6, and 7 "diafiltration volumes (DVs)") with, for example, CWFI.

Optionally, following the step of diafiltering the first retentate solution, the first membrane can be rinsed to recover any residual protein remaining on the retentate side of the first membrane. The residual protein, if any, can then be combined with the second retentate prior to ultrafiltration of the second retentate using the second membrane.

In one embodiment, diafiltering using the first membrane is based on tangential flow technology as described above.

IV. Glycine and/or pH Adjustment

The addition of glycine to the diafiltered solution comprising the protein can provide a beneficial effect on buffering and pH control of the solution being processed, even though the protein itself also may exert buffering capacity. Another benefit of introducing glycine at this stage is reducing or eliminating the creation of aggregate species by effect of any pH adjustment.

Prior to ultrafiltering the second retentate solution comprising the diafiltered protein, the second retentate is formulated with glycine and pH adjusted. Preferably, the pH of the second retentate is adjusted to be below a final target pH (e.g., about 0.25 units below the target pH). In one embodiment, the pH of the second retentate is adjusted to a pH of about 4.2 to about 4.3.

In certain embodiments, a pharmaceutical composition is an aqueous or liquid formulation comprising an acetate buffer of about pH 4.0-5.5, a polyol (polyalcohol), and optionally, a surfactant, wherein the composition does not comprise a salt, e.g., sodium chloride, and wherein the composition is isotonic for the patient.

V. The Second Membrane

Preferably, the step of ultrafiltering the second retentate, which has been formulated with glycine and pH adjusted subsequent to diafiltering, is carried out using an ultrafiltration unit generally comprising of hollow-fiber cartridges of the second membrane, wherein the second membrane has a molecular weight cutoff of about twice the molecular weight cutoff of the first membrane. In one embodiment, wherein the protein is IgG, the molecular weight cutoff of the second membrane is about 100 kDa, wherein the first membrane has a molecular weight cutoff of 50 kDa. In another embodiment, wherein the protein is IgG, the final retentate solution comprises the IgG at the second concentration, wherein the second concentration is at least about twice, three times, four times, or more of the first concentration. In one embodiment, wherein the protein is IgG, the final retentate solution comprises at least about 19% IgG (w/v).

Optionally, the second membrane is rinsed and any residual protein retained by the second membrane is also recovered.

The final retentate solution comprising the concentrated protein can be further processed to a stable liquid formulation. For example, wherein the final retentate solution comprises IgG concentrated in accordance with the present invention, the solution can be further processed to a stable liquid formulation, e.g., as described by U.S. Pat. No. 4,396,608 to Tenold et al., which is incorporated herein by reference in its entirety, or other appropriate final formulation (e.g. a freeze dried formulation). By way of another example for a liquid formulation comprising IgG, the volume of the final retentate comprising the concentrated IgG can be adjusted to yield at least about 16% IgG (w/v), and, optionally, the sterile bulk can be held for a period of time, e.g. not less than 21 days, sufficient to reduce anti-complement activity and/or to inactivate enveloped viruses.

In one embodiment, ultrafiltering using the second membrane is based on tangential flow technology as described above.

The present invention will be illustrated in more detail by way of Examples, but it is to be noted that the invention is not limited to the Examples.

EXAMPLES

Example 1

Purification of IgG from Cohn Fraction II+III Paste

Fraction II+III paste is solubilized in 12 volumes of 5° C. purified water. The mixture pH is adjusted to pH 4.2 with acetic acid, and mixed for 1 hour. This step places the IgG into solution.

The mixture pH is then adjusted up to pH 5.2 with NaOH and sodium caprylate (the "pH swing"). Proteins and lipids are precipitated. The mixture is clarified by filtration to remove precipitate which would interfere with virus inactivation. The caprylate concentration is adjusted to 20 mM at pH 5.1, and the mixture is incubated for 1 hour at 25° C. to effect enveloped virus inactivation.

The mixture is filtered to produce a clear solution for chromatography. The clear solution conductivity is adjusted to between 2.0 and 3.0 mS/cm using purified water. The pH of the clear solution is adjusted to 5.0 to 5.2 following the conductivity adjustment.

Example 2

Chromatography

The clear solution above is applied directly to two anion exchange columns (a strong anion exchanger followed by a weak anion exchanger) linked in series. The IgG flows through the column while impurities (including the caprylate) are bound to the two anion columns Satisfactory purifications are obtained with combinations of Pharmacia Biotech Q & ANX resins and E. Merck TMAE Fractogel.

The clear solution comprising the IgG to be purified is applied directly to the first anion exchanger which is equilibrated with 20 mM sodium acetate at pH 5.1. This is followed by applying the non-binding fraction (the flow through) from the first anion exchange column directly onto a second anion exchange column This column is also equilibrated with 20 mM acetate buffer at pH 5.1. The protein solution is typically loaded onto the first column at a ratio of 50-110 mg IgG/ml packed resin. The protein solution is typically loaded onto the second column at a ratio of 75-95 mg IgG/ml packed resin. The protein to resin ratios is also adjusted beyond these limits, but doing so may have an impact on yield and purity. The protein solution is followed by approximately 2 column volumes of the equilibration buffer, which washes any non-bound IgG off of the columns The unbound fraction comprising highly purified IgG is collected as the solution comprising the plasma product (i.e. IgG) to be concentrated.

Example 3

Two-stage Ultrafiltration/Diafiltration (UF/DF)

The solution comprising the IgG (i.e., the post-chromatography column solution) is concentrated to about 5% IgG (w/v) bulk material using a polyethersulfone C-screen membrane having a molecular weight cutoff of 50 kDa. The concentrated solution temperature is maintained between 2° C. and 12° C. Following diafiltering of the 5% solution with CWFI, the system is rinsed and the recovered material is added to the bulk material. The concentrated solution is then formulated to 0.25M Glycine by adding dry glycine in powder, and the pH is adjusted as needed. The filter membrane performance is not affected (by soiling or clogging) since the protein is only concentrated to 5% (w/v).

Following the formulation step, the 5% solution in 0.25M Glycine is then transferred to a second ultrafiltration unit for further concentration using a hollow fiber membrane having a molecular weight cutoff of 100 kDa. The material is concentrated to at least about 19% IgG (w/v). Prior to final formulation (e.g., adjustment of the liquid formulation to ≥16% IgG (w/v) addition of rinses and pH adjustment, if needed) the IgG solution is sterile filtered.

Example 4

Macrobench Scale Two-stage UF/DF of Q/ANX Column Flow-through

Collected Q/ANX column flow through was concentrated to a concentration of approximately 5% IgG. The material was diafiltered with no less than 7 volumes of water for injection.

The 5% diafiltrate was transferred to a formulation vessel for pH adjustment and addition of glycine. The target established for pH adjustment was 4.15 to 4.25. Adjusting the material within this pH target allowed for a pH of 4.50 (range of 4.0 to 5.0) to consistently be achieved for the sterile bulk material. The pH adjustment solutions included 0.5 M HCl and 0.5 M NaOH.

During the formulation process, dry glycine was added to the post diafiltered material to bring the concentration of the solution to about 0.25 M glycine. The 0.25 M glycine concentration at the pre-final ultrafiltration (UF) stage allowed for the targeted isotonic range of 240-400 mOsm/Kg to be achieved for the sterile bulk material. The pH and glycine parameters established at the pre-final UF stage avoided the need to readjust pH or add additional glycine at points further downstream in the process.

Once the formulation process was completed, the material was filtered through a KWSS Millipore filter, a commercially available 0.5+0.2 micron Milligard filter used to remove any debris prior to final concentration with the Koch hollow fiber cartridges (Koch Membrane Systems, Inc., Wilmington, Mass.). Glycine formulated material was filtered through the KWSS filter and into the ultrafiltration (UF) feed vessel for the Koch Hollow fiber cartridges. Upon completion of filtration, a glycine rinse buffer was used to flush out the formulation vessel, tubing, and filter in order to recover residual protein material. The glycine buffer used throughout the process was 0.25 M glycine adjusted to a pH target of 4.0 to 5.0.

The final UF concentration step was completed with the use of Koch hollow fiber cartridges (Model # CTG.1"HF1.0-43-PM100-PB). The scale used for development/macrobench work was 0.1 m² of membrane area. Formulated material was concentrated to approximately 20%. The feed pressure range established for the process was 25 to 27 psig (target: 26 psig). The retentate pressure range was 10 to 12 psig (target: 11 psig). The temperature range was 2° C. to 20° C.

A glycol bath was used to control temperature. During the end of the final concentration stage, where retentate material became more viscous, process temperatures reached temperatures of 18° C. but never exceeded 20° C. No adverse conditions were observed while operating at the higher end of the 2° C. to 20° C. range.

After the material was concentrated to approximately 20%, the system was drained and then rinsed with 0.25 M glycine buffer in order to recover residual protein. The rinse method used was a single pass flush with a specified amount of 0.25 M Glycine buffer. The amount of rinse can be dependent on the scale of the process and can be limited to a volume that will not over dilute the in-process material. The desired concentration for the diluted UF concentrate was 18%. This target concentration allowed for the use of additional rinse buffer at the Initial Sterile Bulk (ISB) and Final Sterile Bulk (FSB) stages of the process. Two separate rinses were performed on the system after concentration. The largest amount of residual protein was recovered during the first rinse. Rinses 1 and 2 were added back to the UF concentrate material in order to bring the concentration to approximately 17.5%.

The diluted UF concentrate was then mixed and sterile filtered using a Millipore Express Sterile High Capacity (SHC) filter. Options for pre-clinical, clinical and commercial production sterile filtration include the use of an autoclavable or gamma irradiated version of the SHC filter. Also ISB may be combined and sterile filtered into a larger final sterile bulk. Combining bulks to deliver to the Sterile Filling Facility (SFF) will decrease the yield loss for filling operations.

Upon completion of filling operations, material can be put on incubation at 23° C. to 27° C. (target: 24° C.) for a minimum of 21 days and not to exceed 28 days. The incubation procedure can remain the same or be changed depending on, for example, viral validation results.

Example 5

Evaluation of Filtration Cassettes

The scale used for development/macrobench work was 0.1 m² of membrane area and UF/DF operational temperature range was 2° C. to 20° C. In-process material from an IGIV production process was used. The starting material included Q/ANX column flow through, 5% pre diafiltration, and 5% post diafiltration materials.

Cassettes evaluated included Millipore 50 kD and 100 kD cassettes along with different screen options. 70 kD filters (Pall Inc., East Hills, N.Y.) were also examined. The optimal Trans Membrane Pressure (TMP) determined for Millipore 100 kD cassettes was 15 psig (Feed pressure 25 psi and Retentate pressure 5 psi). The optimal Trans Membrane Pressure (TMP) determined for Millipore 50 kD cassettes was 17.5 psig (Feed pressure 25 psi and Retentate pressure 10 psi). The optimal Trans Membrane Pressure (TMP) determined for Pall 70 kD cassettes was 20 psid (Feed pressure 20 psi and Retentate pressure 10 psi).

Example 6

Purification of IgG from Cell Culture Medium

Cell line growth media containing secreted monoclonal antibodies is first adjusted to the proper pH and conductivity. This is accomplished by diafiltering against purified water while adjusting the pH to 4.2 with acetic acid. The solution conductivity is adjusted to less than 1.0 mS. Purification and concentration of the monoclonal antibody is achieved by following the steps above.

Example 7

Effect of Various Parameters on Viscosity, Aggregate Formation, Fragmentation, and Dimer Formation Based on generated data, it was found that increasing the amount of glycine in the formulation did not affect the achieved final protein concentration. The approximately same higher protein concentration solution can be achieved by formulating the solution using glycine in a range between 0.05 M and 0.3 M. When the concentration of the protein solution is made in presence of water instead of glycine, the final protein solution is approximately 3-4% w/v units less concentrated.

Moreover, there was no change in the viscosity of a IgG protein solution when it was formulated with glycine within the range of 0.05 M to 0.5 M. For example, the viscosities of various formulations of IgG solutions, with a concentration of 16% w/v and pH 4.2, between 0.2 M to 0.5 M glycine, remained at about 7.9 centipoise (cP) (see, e.g., FIG. 2).

Figure 1:
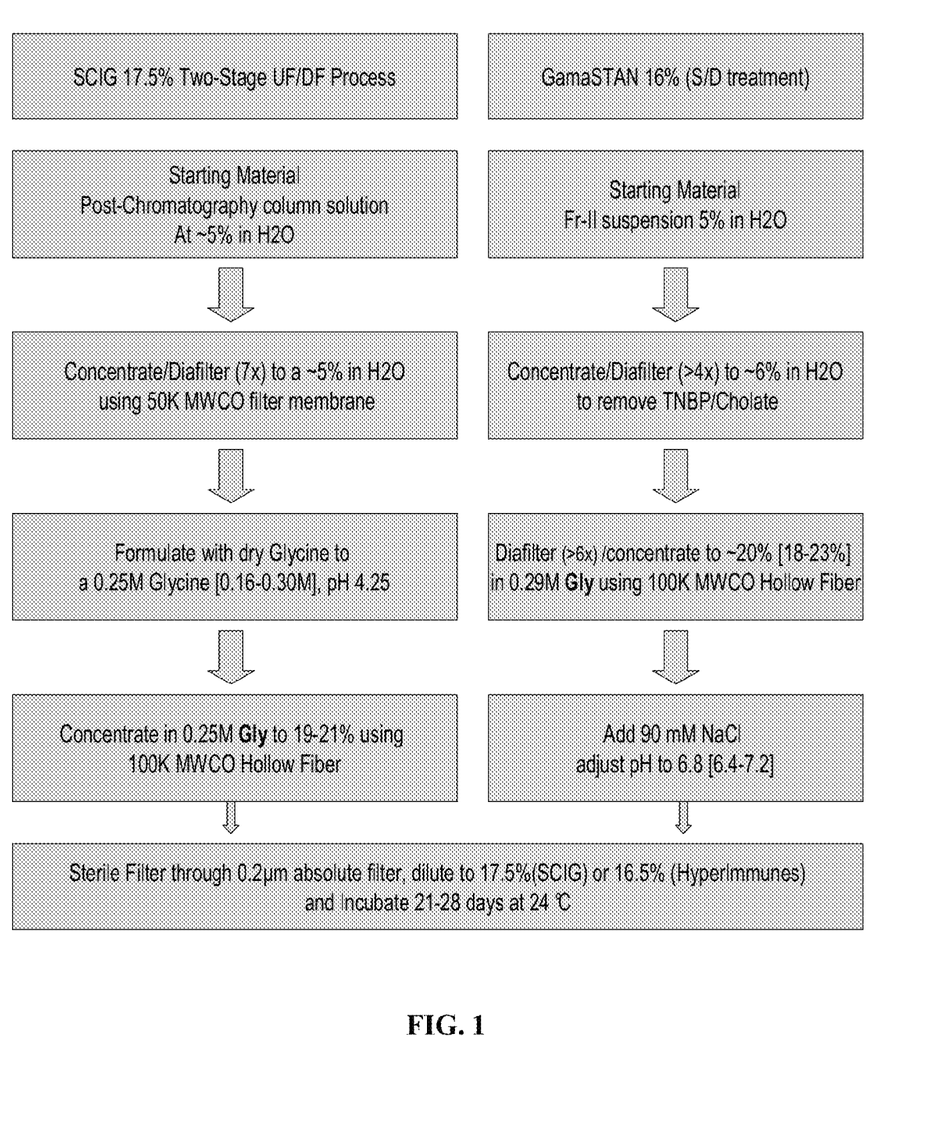
FIG. 1 is an example illustrating some embodiments of a process flow diagram schematically depicting a two stage ultrafiltration/diafiltration method for producing high IgG concentration formulation. A, scheme based on ion exchange chromatography; and B, scheme based on solvent/detergent (S/D) treatment.
Figure 2:
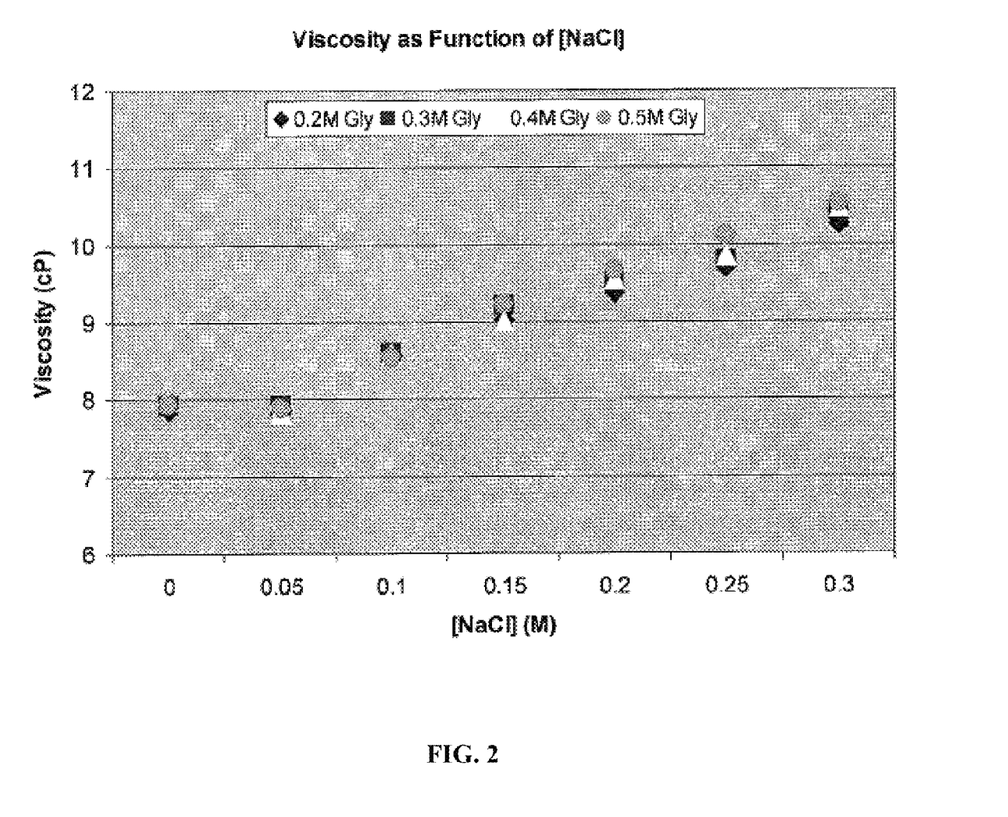
FIG. 2 shows viscosity of a protein solution as a function of salt concentration.

Further, others have proposed that addition of NaCl to a formulation buffer can appreciably decrease the viscosity of a solution. In the example presented here, with plasma derived antibodies (IgG), the addition of NaCl in the formulation buffer, in amounts anywhere from 0.05 M to 0.3 M, increased the viscosity of the protein solution by up to 2.6 cP (from 7.9 cP—without NaCl— to 10.5 cP with 0.3 M NaCl, in a 16% w/v in 0.2M glycine, pH 4.2 IgG solution) (FIG. 2).

Figure 3:
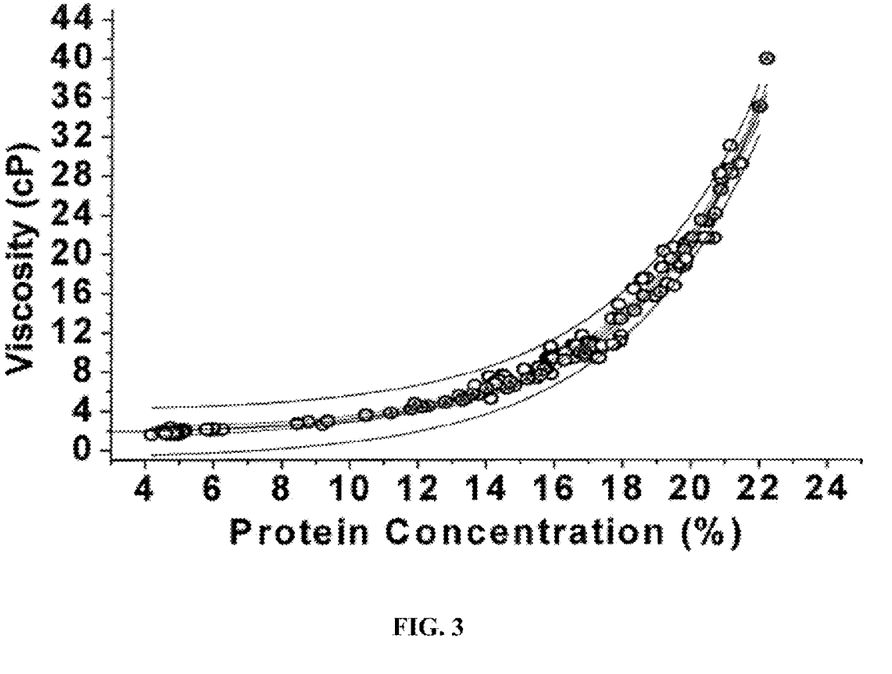
FIG. 3 shows viscosity of a protein solution as a function of protein concentration.
Figure 4:
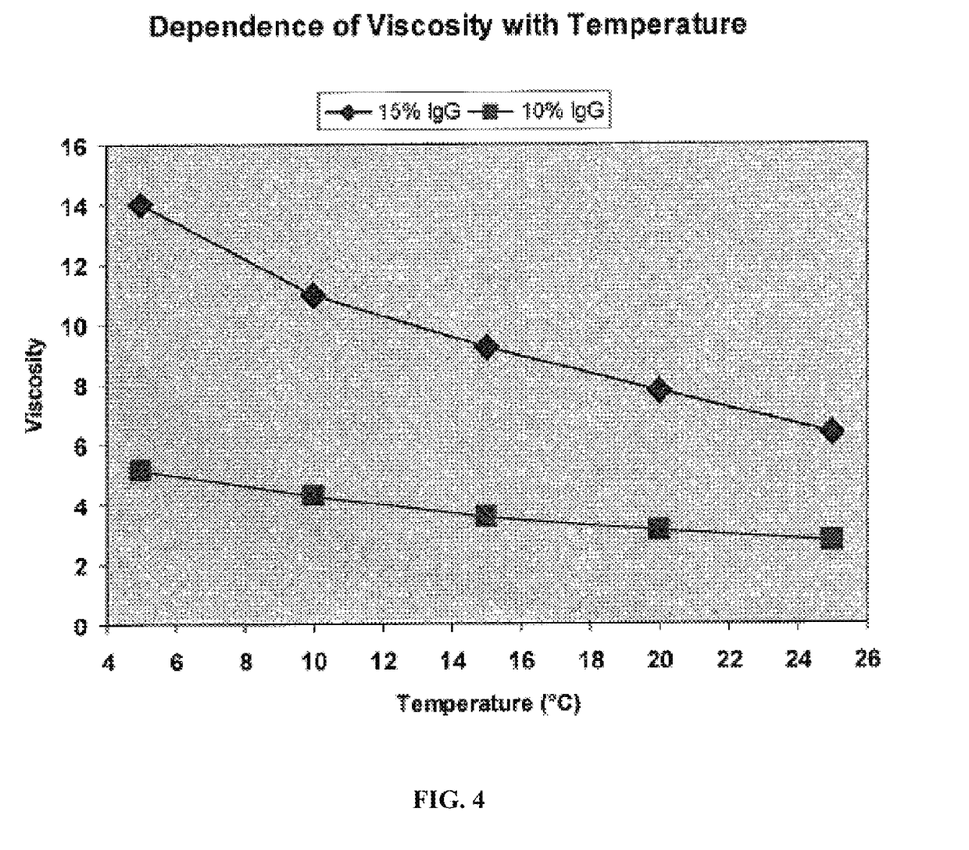
FIG. 4 shows viscosity of a protein solution as a function of temperature.

As shown in FIG. 3, the viscosity of a protein solution can be expressed as a polynomial function of 3rd order, dependent on the protein concentration. To determine the dependence of viscosity with temperature, two protein concentrations were tested having the same pH and buffer composition. As shown in FIG. 4, the dependence of the viscosity with the temperature is affected by the protein concentration (e.g., there is a more pronounced dependence of viscosity for the sample at higher concentration than for the diluted product).

Figure 5:
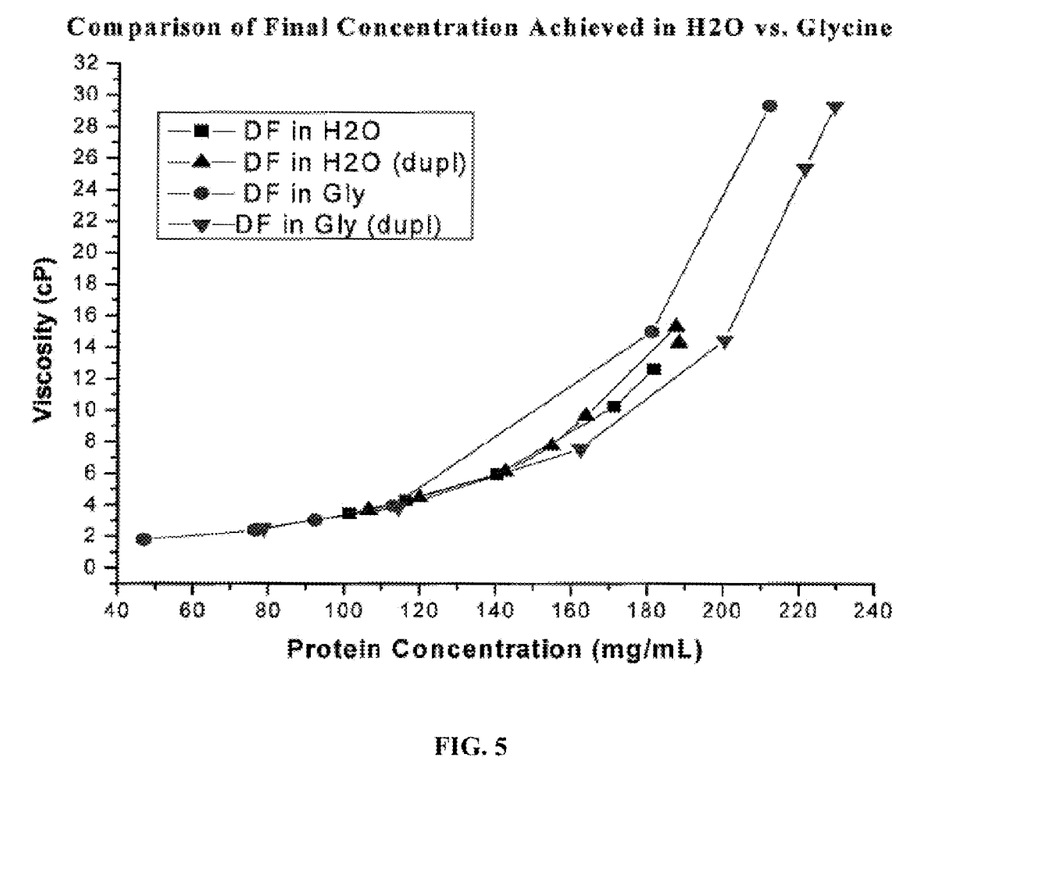
FIG. 5 shows viscosity of a protein solution as a function of protein concentration.

Moreover, the presence of glycine enabled reaching higher protein concentrations. The endpoint concentration achieved in the presence of either water or glycine is shown in FIG. 5 (DF=diafiltered) where the presence of glycine is shown to allow for reaching a much higher final protein concentration. The pH of the solution was kept the same for both processes (around 4.2), while the viscosity measurements were always performed at 20° C. The end point concentration was reached when the retentate flow in the UF/DF system stopped.

Figure 6:
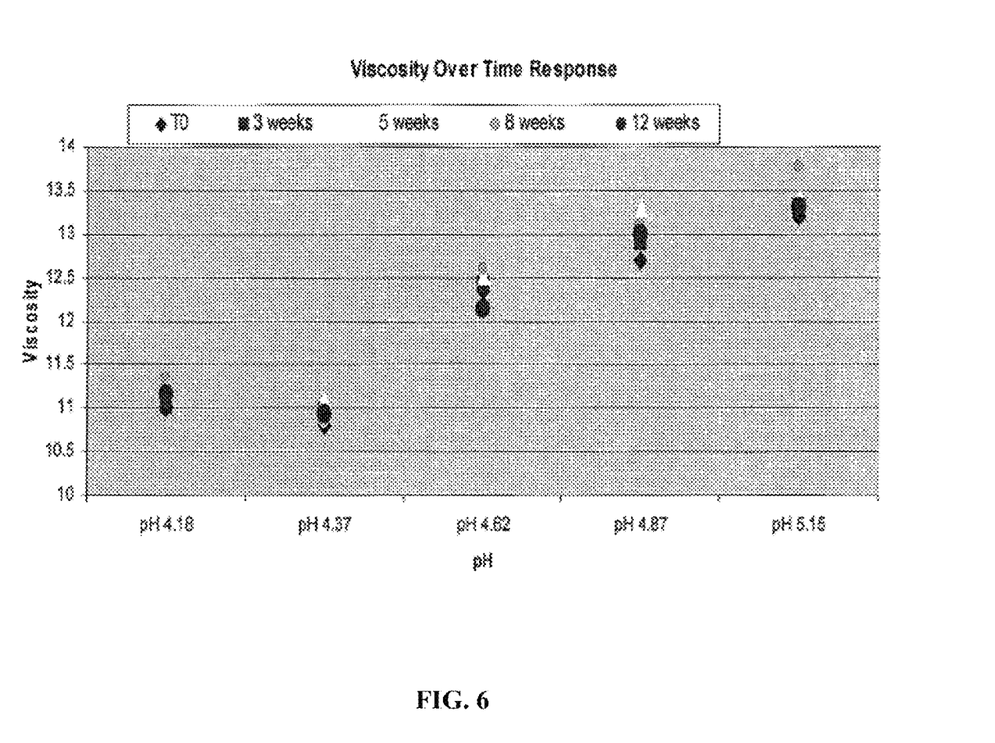
FIG. 6 shows viscosity of a protein solution as a function of pH for various times.
Figure 7:
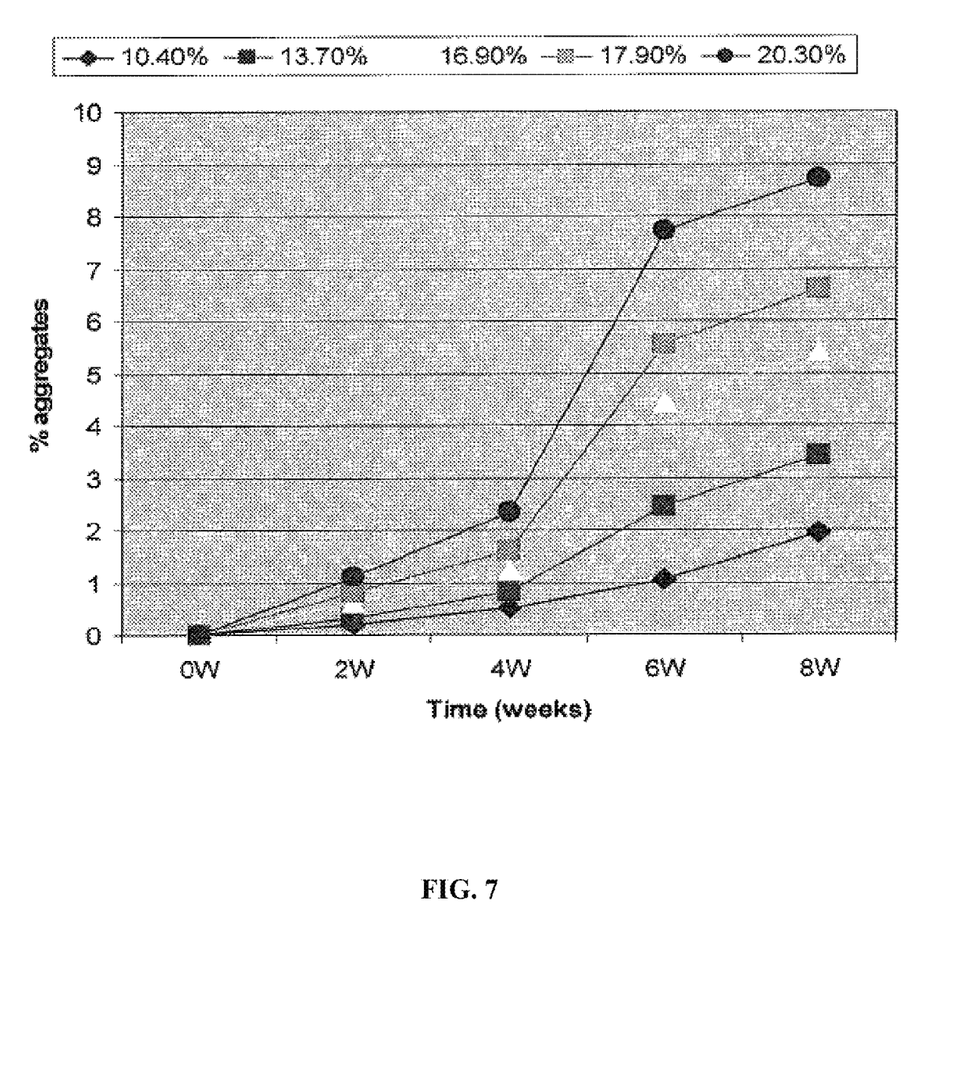
FIG. 7 shows extent of aggregate formation as a function of time for various protein concentrations.
Figure 8:
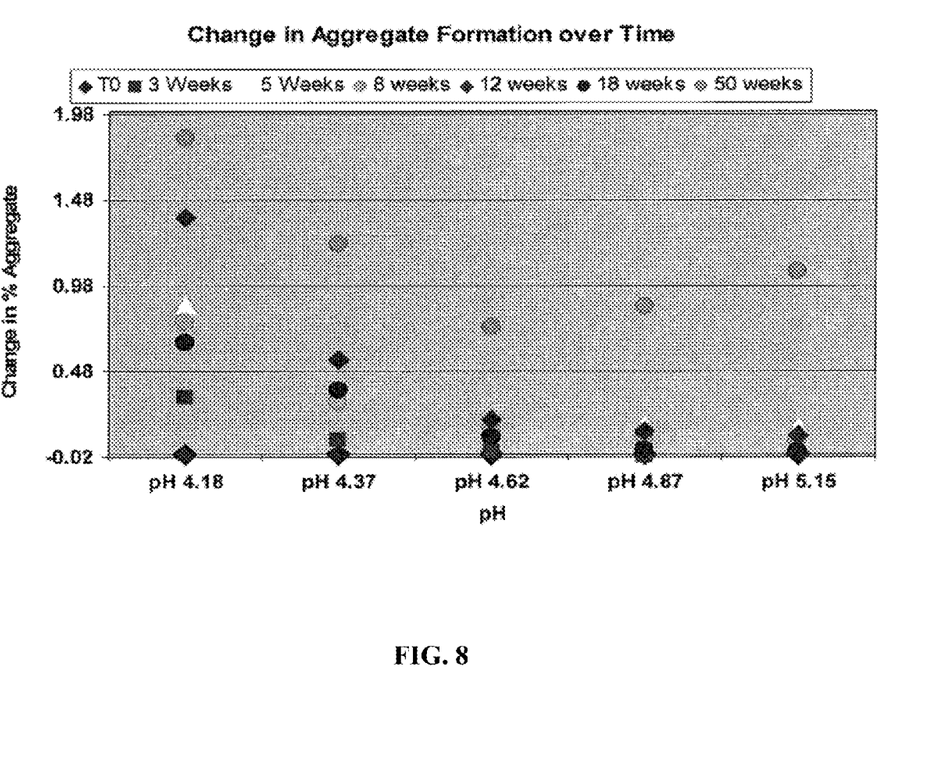
FIG. 8 shows change in aggregate formation as a function of pH for various times.

Moreover, the dependence of viscosity as function of the pH of the protein solution is shown in FIG. 6 for a series of solutions containing equal protein concentrations (17% w/v). Over time, the viscosity for the sample did not change, remaining almost within the same value, except for the normal variations expected by handling high protein concentration solutions under experimental measuring conditions. On the other hand, it is believed that aggregate formation is at least dependent on protein concentration, under similar temperature, pH and buffer composition conditions. Accordingly, FIG. 7 shows the results of experiments conducted at various protein concentrations, and aimed to assess the extent of aggregate formation under controlled conditions. And, FIG. 8 shows the dependence of aggregate formation with the pH of the formulation for various samples containing the same protein concentration (17% w/v) and buffer composition (0.2 M Gly), over the period of one year. These results at least suggested that the aggregate formation can be repressed by the pH of the formulation. Higher pH formulations can be less favorable to aggregate formation.

Figure 9:
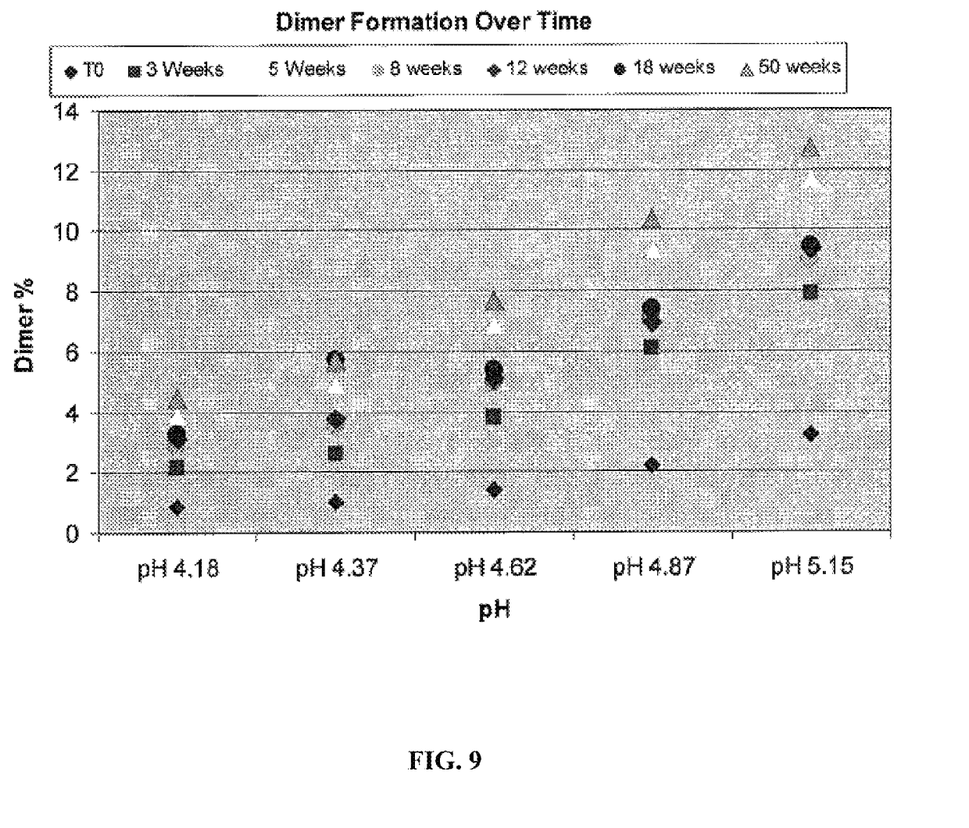
FIG. 9 shows dimer formation as a function of pH for various times.

Moreover, shown in FIG. 9, the level of dimers present correlated with the increase in the pH of the formulations. For a series of samples under similar conditions of protein concentration, buffer composition and temperature, the population of dimer present in a sample can be roughly tripled by modifying the pH of the formulation by 1 unit. Also the dimerization level changed over time in a predictable manner, as function of the pH and time elapsed during storage.

Figure 10:
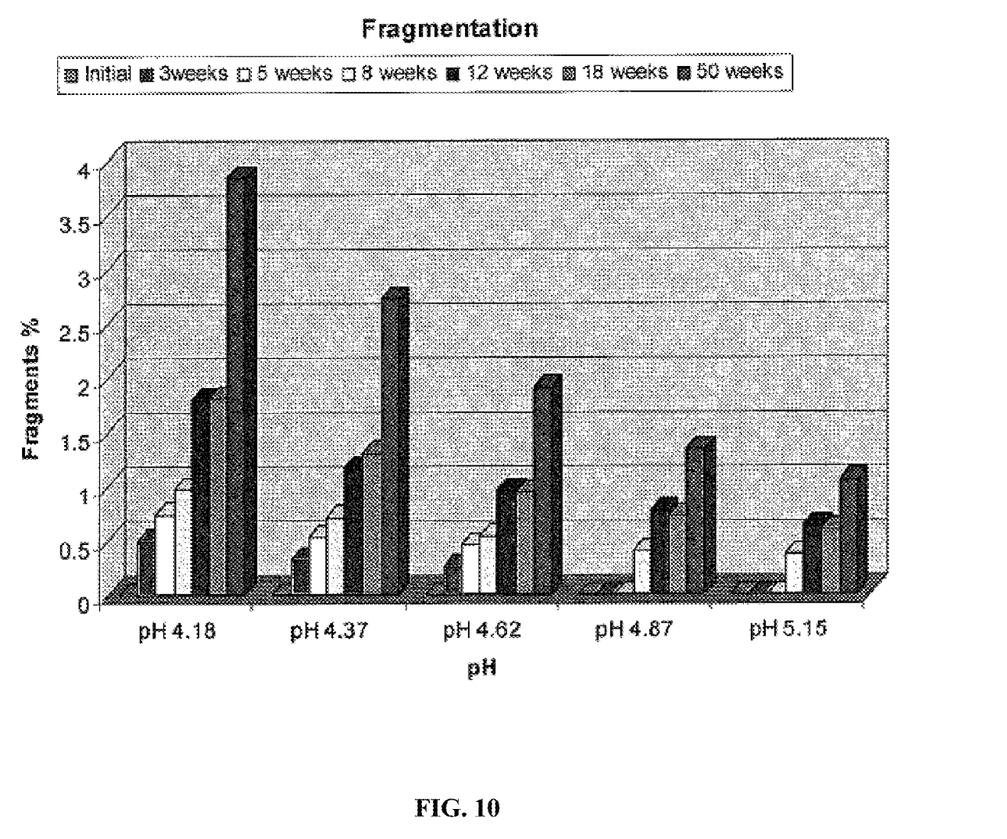
FIG. 10 fragmentation of a protein as a function of pH for various times.

Finally, by controlling the pH of the protein solution, the fragmentation levels of the IgG molecule can be manipulated. FIG. 10 shows the time-elapsed (up to one year) response of the fragmentation of IgG molecules in a 17% (w/v) solution stored at 25° C. as function of the pH. In addition to retarding the appearance of fragments, an increase in pH also decreased the actual formation rate of fragments.

What is claimed is:

1. A method for concentrating a plasma product of a solution comprising a protein, the method comprising:
    a) ultrafiltering the solution using a first membrane to form a first retentate solution comprising the protein at a first concentration, wherein the first membrane has a molecular weight cutoff sufficient to retain at least a portion of the protein present in the solution;
    b) diafiltering the first retentate solution with an aqueous solution using the first membrane to form a second retentate solution comprising the protein at about the first concentration;
    c) formulating the second retentate solution comprising the diafiltered protein, with glycine and adjusting the pH to form a formulated second retentate solution; and
    d) ultrafiltering the formulated second retentate solution of step c) using a second membrane to form a final retentate solution comprising the protein at a second concentration, wherein the second membrane has a molecular weight cutoff greater than the molecular weight cutoff of the first membrane, wherein the second concentration is greater than the first concentration.

2. The method of claim 1, wherein the protein is IgG.

3. The method of claim 1, wherein the first membrane is a polyethersulfone C-screen membrane having a molecular weight cutoff of 50 kDa.

4. The method of claim 1, wherein the first concentration is about 5% protein (w/v).

5. The method of claim 1, wherein the second membrane is a hollow fiber membrane or a cassette.

6. The method of claim 1, wherein the second membrane has a molecular weight cutoff of 100 kDa.

7. The method of claim 1, wherein the second concentration is at least about 19% protein (w/v).

8. The method of claim 1, wherein the first membrane has a molecular weight cutoff sufficient to retain at least 90% of the protein present in the solution.

9. The method of claim 4, wherein, in step c), the about 5% diafiltered protein is formulated to about 0.16 to about 0.30 M glycine and the pH is adjusted to about 4.3.

10. A method for concentrating a protein of a solution comprising the protein, the method comprising:
    a) ultrafiltering the solution using a first membrane to form a first retentate solution comprising the protein at a first concentration of about 5%, wherein the first membrane has a molecular weight cutoff sufficient to retain at least about 90% of the protein;
    b) diafiltering the first retentate solution using the first membrane with water to form a second retentate solution comprising the protein at about the first concentration;
    c) formulating the about 5% diafiltered protein of step b) to about 0.16 to about 0.30 M glycine, wherein the formulating further comprises adjusting pH to about 4.3; and
    d) ultrafiltering the second retentate solution using a second membrane to form a final retentate solution comprising the protein at a second concentration of about 19 to about 21%, wherein the second membrane has a molecular weight cutoff greater than the molecular weight cutoff of the first membrane, wherein the second concentration is greater than the first concentration.

11. The method of claim 10, wherein the protein is IgG.

12. The method of claim 11, wherein the first membrane has a molecular weight cutoff of about 25 kDa to about 75 kDa.

13. The method of claim 10, wherein the first membrane has a molecular weight cutoff of about 50 kDa, wherein the second membrane has a molecular weight cutoff of about 100 kDa.

14. The method of claim 10, wherein the second membrane is a hollow fiber membrane or a cassette.

15. A method for concentrating a plasma product of a solution comprising a protein, the method comprising:
    a) ultrafiltering the solution below about 20° C. using a first membrane to form a first retentate solution comprising the protein at a first concentration, wherein the first membrane has a molecular weight cutoff sufficient to retain at least a portion of the protein present in the solution;
    b) diafiltering the first retentate solution below about 20° C. with an aqueous solution using the first membrane to form a second retentate solution comprising the protein at about the first concentration;

c) formulating the second retentate solution comprising the diafiltered protein, by adding glycine and adjusting the pH to form a formulated second retentate solution; and d) ultrafiltering the formulated second retentate solution of step c) below about 20° C. using a second membrane to form a final retentate solution comprising the protein at a second concentration, wherein the second membrane has a molecular weight cutoff greater than the molecular weight cutoff of the first membrane, wherein the second concentration is greater than the first concentration.

* * * * *